United States Patent [19]

Stoltz

[11] Patent Number: 5,458,009
[45] Date of Patent: Oct. 17, 1995

[54] ENAMELED TUBULAR UNIT

[75] Inventor: Bruno Stoltz, Herxheim, Germany

[73] Assignee: Pfaudler-Werke GmbH, Schwetzingen, Germany

[21] Appl. No.: 206,795

[22] Filed: Mar. 7, 1994

[30] Foreign Application Priority Data

Mar. 12, 1993 [EP] European Pat. Off. ............ 93104022

[51] Int. Cl.$^6$ .................................................. G01N 1/14
[52] U.S. Cl. ........................................ 73/863.83; 138/114
[58] Field of Search .................... 73/863.81–863.83, 73/863.85, 863.86, 866.5; 374/157, 208; 138/114, DIG. 3, DIG. 6, 109; 285/45

[56] References Cited

U.S. PATENT DOCUMENTS

| | | | |
|---|---|---|---|
| 3,623,369 | 11/1971 | Kjellberg | 374/157 |
| 3,747,411 | 7/1973 | McDermott et al. | 73/863.85 |
| 4,166,020 | 8/1979 | Trampert | 204/195 R |
| 4,329,937 | 5/1982 | Holland . | |
| 4,335,753 | 6/1982 | Flye | 138/109 |
| 4,368,219 | 1/1983 | Nagata et al. . | |
| 4,594,903 | 6/1986 | Johnson | 73/863.83 |
| 5,109,711 | 5/1992 | Wendt | 73/863.11 |

FOREIGN PATENT DOCUMENTS

| | | |
|---|---|---|
| 0430021A2 | 6/1991 | European Pat. Off. . |
| 2133419 | 7/1971 | Germany . |
| 3818957A1 | 12/1989 | Germany . |

OTHER PUBLICATIONS

Leaflet by Applicant dated Apr. 30, 1991, 177–8 def.
Leaflet: pHampler of Ethylene Corporation.
Leaflet: Sampling device of De Dietrich.
Chemical Processing: "Automated pH control boosts reactor efficiency".
Pfaudler Sales Bulletin SB21-400-1.
Leaflet: "Sampling device" of Neotecha.

*Primary Examiner*—Robert Raevis
*Attorney, Agent, or Firm*—Michael L. Dunn

[57] ABSTRACT

Enameled tubular unit which can be inserted into and fixed at the nozzle of a vessel and which is enameled at all places exposed to the product and can be used as dip pipe. The unit is having a double wall formed by two coaxial tubes (1,2) connected at the lower end through a connecting region with each other. The outer surface of the outer tube (1), the inner surface of the inner tube (2) and the connection region are enameled. The diameter of the outer tube is selected in accordance with strength considerations in such a manner, that it permits performing an additional function of the unit. Into the inner tube (2) a sampling tube (3) is inserted, consisting of a material having a corrosion resistance corresponding to the corrosion resistance of enamel. The outer tube may be a component part of a thermometer tube or of an agitation baffle. The outer tube may also serve as a measuring probe carrier.

12 Claims, 1 Drawing Sheet

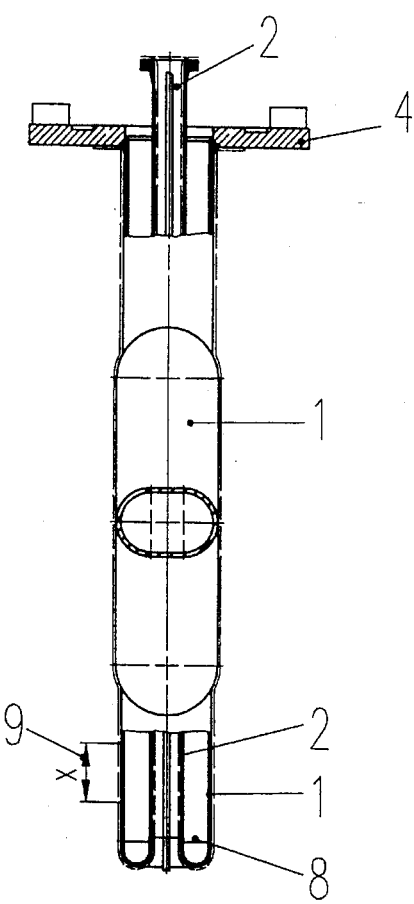
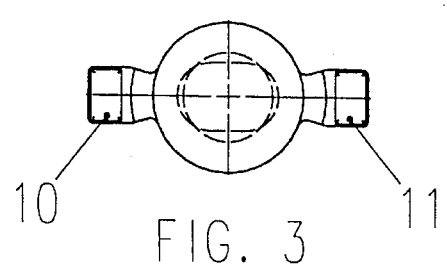
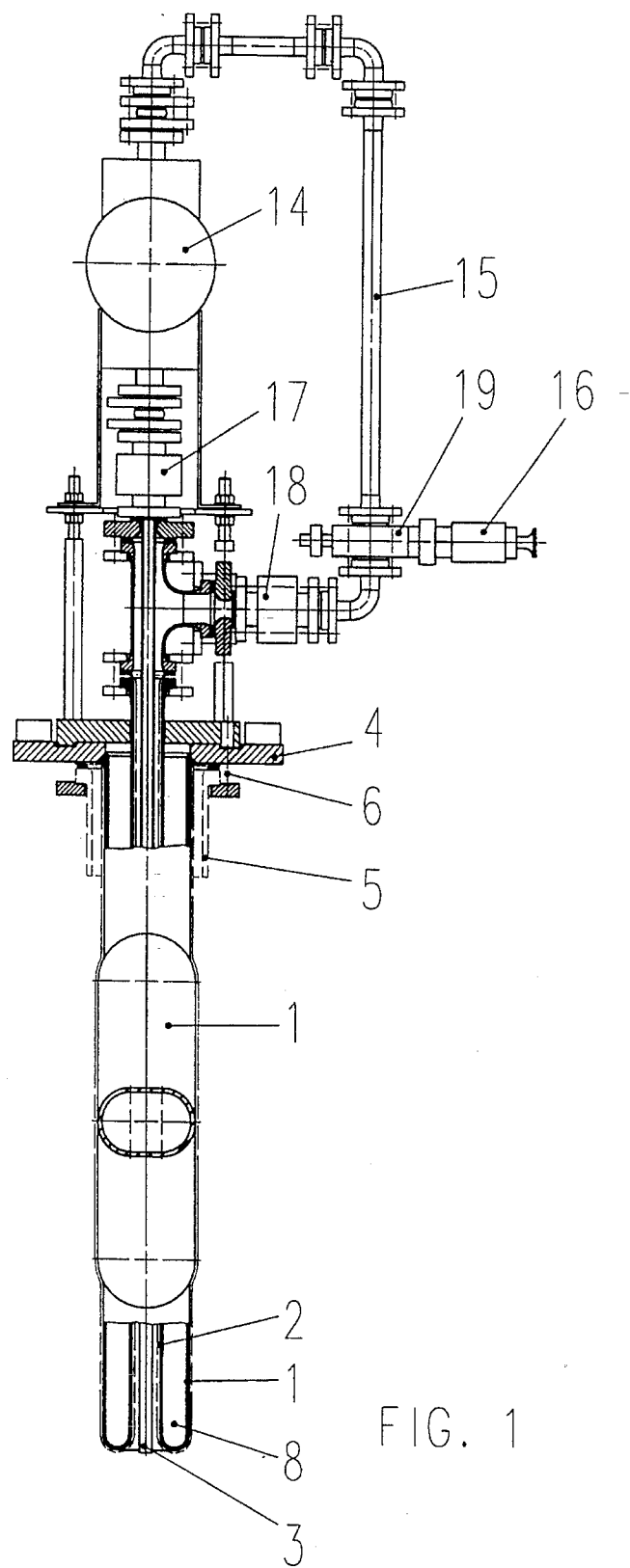

5,458,009

ENAMELED TUBULAR UNIT

BACKGROUND OF THE INVENTION

The invention relates to an enameled tubular built-in unit which can be inserted into and fixed at the nozzle of a container and which is enameled at all places exposed to the product and is usable as a dip pipe.

Enameled built-in units of this kind are known which can be inserted through a nozzle of an enameled reactor comprising an agitator and may have an inner diameter between 25 and 200 mm and a total length between about 850 and 3150 mm and may be used to introduce or to press out liquids or to attack with gas.

For reactors used in the chemical and pharmaceutical industry often means for sampling during operation are used. As tubes for sampling usual dip tubes may be used. Known embodiments of such dip tubes bring about the disadvantage, that specifically for the sampling tube a nozzle at the container is necessary. However, in the case of enameled reactors the number of nozzles is limited. Furthermore, in the case of enameled reactors containing an agitator the number and size of the nozzles is standardized in the most cases. The number of nozzles often cannot be increased out of design reasons. Therefore it is desirable that the sampling tube could be combined with another unit. In this connection it is already known to design a temperature detection unit in such a manner, that it can be inserted in and removed from an enameled built-in unit, which may be an agitation baffle (DE 38 18 957 A1).

If one tries to combine an enameled dip tube with another enameled built-in unit, the difficulty arises, that the demands and the design criteria, resp., of such built-in units are very different. Agitation baffles normally must have larger cross sections in order to cause the necessary agitation effect and to withstand static and dynamic loads. On the other hand, the cross sections of the suction and flow-off conduits of a sampling system should be as small as possible, in order to keep the displacement amounts of the pump small and in order to avoid settling in the conduits, e.g. in the case of suspensions.

BRIEF DESCRIPTION OF THE DRAWINGS

FIG. 1 illustrates, in longitudinal section, a sampling system with an enameled unit in accordance with the invention;

FIG. 2 illustrates another embodiment of a unit in accordance with the invention, which is partially shown in section; and FIG. 3 illustrates a plan view of the embodiment in FIG. 2.

BRIEF DESCRIPTION OF THE INVENTION

It is therefore an object of the invention to provide for an enameled unit of the above mentioned type which can be also used for sampling, but which avoids disadvantages and difficulties of the mentioned type as far as possible. No changes of the design of the enameled container shall be necessary and it shall be avoided normally, that a nozzle has to be used exclusively for the sampling device. All parts which come into contact with the product shall be enameled or have a corresponding protection against corrosion.

This problem is solved by the present invention. The present invention comprises an enameled tubular unit, which can be inserted into and fixed at a nozzle of a container and which is enameled at all places exposed to product held by the container and is usable as a dip pipe, characterized in that the built-in unit has a double wall formed by an outer tube (1) and an inner tube (2) connected with each other at a first end of the unit by means of an enameled connecting region, the outer tube (1) having an enameled outer surface, and the inner tube (2) having an enameled inner surface, the outer tube (1) having a diameter and strength which permits a function in addition to holding the inner tube (2).

With a unit in accordance with the invention it is possible to combine substantially any cross sections and functions. As an example, in the case of a combination with an agitation baffle the outer tube can be designed in accordance with the function of the baffle, whilst the cross section of the inner tube can be designed freely in accordance with the demands of the circulation for sampling.

Furthermore, the unit in accordance with the invention may be provided with various measuring probes, e.g. for the measurement of the temperature or for the measurement of the pH-value in the container, so that a single unit e.g. the functions of a baffle, sampling tube, measuring probe carrier, feeding tube or dip tube can be realized.

DETAILED DESCRIPTION OF THE INVENTION

The invention will be described by way of example with reference to the accompanying drawings.

The sampling system shown in FIG. 1 comprises a built-in unit in accordance with the invention, which can be mounted in a nozzle 5 shown in dashed lines, which nozzle is provided at an enameled reactor vessel (not shown) containing an agitator system. A tube 1 enameled on its outer surface is inserted into the vessel. In this tube a second tube 2 is coaxially arranged, which is connected at its lower end with the outer tube and is also enameled on its inner surface. The connection of the two tubes on the lower end is designed in such a manner, that the region of connection can be enameled. Within the tube 2 a sampling tube 3 is arranged made out of a material, having a corrosion resistance substantially corresponding to the corrosion resistance of enamel. Preferably the material of the sampling tube is PTFE. It is advantageous to provide the sampling tube 3 with an outer diameter which is substantially smaller than the inner diameter of the inner tube 2, in order that the displacement of a circulating pump 14 provided at the sampling system can be made rather small. The circulating pump 14 has a design which is corrosion resistant on all surfaces coming in contact with the product. The pump may be e.g. a diaphragm pump which is lined with PTFE and is provided with a diaphragm out of PTFE.

In the embodiment of a built-in unit in accordance with the invention as shown in FIGS. 1 to 3, at the upper end of the outer tube 1 a mounting flange 4 is provided, which can be fixed at a nozzle 5 on the vessel by means of a screw flange connection 6.

The tubes 1, 2 and 3 are arranged coaxially. Since the built-in unit 1, 2, 4 is connected by a loose flange with the nozzle 5 and the mounting with the elements 14 to 19, it is possible in the case of a baffle to turn the baffle for any angle without the necessity to turn also the mounting.

As may be seen from FIGS. 1 and 2, the outer tube 1 may be designed as a baffle in order to allow for a further function.

With the built-in unit in accordance with the invention substantially any cross sections and functions may be combined. Whilst in the embodiment as shown in FIG. 2 the outer tube 1 may be designed in accordance with the function as a baffle, the cross section of the inner tube may be designed freely under consideration of the demands of the circulation for sampling.

The outer tube 1 preferably performs the additional function of a thermometer tube, since in the space 8 between the outer and the inner tube means for a temperature measurement can be arranged. Furthermore, the outer tube 1 may serve as a measuring probe carrier, as an example by providing on the outer surface of the enamel of the outer tube 1 a reference electrode region 9 out of pH-sensitive enamel, which reference electrode out of enamel is connected with a known but not shown measuring electrode (DE 21 33 419 C2).

In order to perform a temperature measurement, a thermoelement may be embedded into the enamel layer of the outer tube 1. The temperature can also be measured by means of a resistance thermometer, which is embedded into the enamel layer on the outer surface of the baffle. A further possibility is to be seen in the fact, that means are provided at the baffle for continuously monitoring during the production, if damages of the enamel layer, leaky tantalum plugs or leakages at gaskets occur in an initial state. For this purpose the baffle can be provided with a measuring and control electrode out of rhodium (leaflet 177-8 def of Apr. 30, 1991 of the applicant).

As may be seen from FIGS. 2 and 3, connectors 10 and 11 are provided for the measuring probes, if the baffle is combined with measuring probes.

The sampling system as shown in FIG. 1 contains, besides the mentioned circulating pump, a circulating conduit 15 and valves 17, 18 and 19 provided therein. If a three-way valve is inserted into the circulating conduit 15, it is possible to introduce through this valve product components, so that the sampling tube can also be used as a feeding tube.

During operation the circulating pump 14 is continuously driven. The pump draws off product though the sampling tube 3, as indicated by the upwardly directed arrow at the lower end of the tube 3. The product is conveyed through the circulating conduit 15 passing the sampling valve 16 and through the annular space between the inner tube 2 and the sampling tube 3 back to the vessel, as indicated by the downwardly directed arrow at the lower end of the built-in unit. If a sample shall be drawn off, the sampling valve 16 is opened to the product side and the sampled quantity of liquid is fed into a bottle. By continuously pumping it is guaranteed, that the composition of the product at the sampling valve 16 is always identical with the composition of the product in the enameled vessel provided with an agitator system.

What is claimed is:

1. An enameled tubular unit, which can be inserted into and fixed at a nozzle of a container and which is enameled at all places exposed to product held by the container and is usable as a dip pipe, characterized in that the unit has a double wall formed by an outer tube (1) and an inner tube (2) connected with each other at a first end of the unit by means of an enameled connecting region, the outer tube (1) having an enameled outer surface, and the inner tube (2) having an enameled inner surface, the outer tube (1) having a diameter and strength which permits a function in addition to holding the inner tube (2).

2. The enameled tubular unit as claimed in claim 1 characterized in that a sampling tube (3) is arranged within the inner tube (2), said sampling tube consisting of a material having a corrosion resistivity corresponding to that of enamel, the sampling tube (3) having an outer diameter which is smaller than the inner diameter of the inner tube (2).

3. An enameled tubular unit as claimed claim 2, characterized in that the inner tube (2) protrudes over an upper surface of a mounting flange (4) provided at an upper end of the unit.

4. An enameled tubular unit as claimed in claim 2, characterized in that the material of the sampling tube (3) is PTFE.

5. An enameled tubular unit as claimed in claim 2, characterized in that the outer tube (1) is the shaft of a baffle.

6. An enameled tubular unit as claimed in claim 2, characterized in that the outer tube (1) is a portion of a thermometer tube, and means for measuring temperature are arranged in a space (8) between the outer and inner tubes (1,2).

7. An enameled tubular unit as claimed in claim 1, characterized in that the outer tube (1) is the shaft of a baffle.

8. An enameled tubular unit as claimed in claim 7, characterized in that the outer tube (1) is a portion of a thermometer tube, and that in a space (8) between the outer and the inner tube (1,2) means for measuring temperature are arranged.

9. An enameled tubular unit as claimed in claim 7, characterized in that the inner tube (2) protrudes over an upper surface of a mounting flange (4) provided at an upper end of the unit.

10. An enameled tubular unit as claimed in claim 1, characterized in that the outer tube (1) is a portion of a thermometer tube, and means for measuring temperature are arranged in a space (8) between the outer and inner tubes (1,2).

11. An enameled tubular unit as claimed in claim 1, characterized in that a measuring electrode region (9) is provided on the outer tube (1) which electrode protrudes from an enameled surface of the outer tube.

12. An enameled tubular unit as claimed in claim 1, characterized in that the inner tube (2) protrudes over an upper surface of a mounting flange (4) provided at an upper end of the unit.

* * * * *

UNITED STATES PATENT AND TRADEMARK OFFICE
CERTIFICATE OF CORRECTION

PATENT NO. : 5,458,009
DATED : October 17, 1995
INVENTOR(S) : Bruno Stoltz, et al.

It is certified that error appears in the above-identified patent and that said Letters Patent is hereby corrected as shown below:

On the title page, item [75] Inventors, should read;

--
    Bruno Stoltz, Herxheim, Germany;
    Karl Dieter Rumpf, Speyer, Germany;
    Reinhart Schertz, Oftersheim, Germany; and
    Siegfried Wolf, Gauangelloch, Germany Signed and Sealed this Second Day of December, 1997

*Attest:*

BRUCE LEHMAN

*Attesting Officer*      *Commissioner of Patents and Trademarks*